United States Patent [19]
Freeman

[11] Patent Number: 5,968,024
[45] Date of Patent: Oct. 19, 1999

[54] OSTOMY APPLIANCE AND WOUND DRAINAGE DEVICE WITH SELF ADHERING DRAIN SYSTEM

[75] Inventor: Frank Freeman, Abaco, Bahamas

[73] Assignee: E. R. Squibb & Sons, Inc., Princeton, N.J.

[21] Appl. No.: 09/028,340

[22] Filed: Feb. 24, 1998

[51] Int. Cl.⁶ ........................................... A61F 5/44
[52] U.S. Cl. ..................... 604/334; 604/332; 604/323
[58] Field of Search .................................. 604/332, 334, 604/335, 323, 350, 342

[56] References Cited

U.S. PATENT DOCUMENTS

| 3,690,320 | 9/1972 | Riely ........................................ 604/333 |
| 3,825,005 | 7/1974 | Fenton ..................................... 604/332 |

*Primary Examiner*—Mark O. Polutta
*Attorney, Agent, or Firm*—Waton & Kipnes, P.C.

[57] ABSTRACT

An ostomy appliance or wound drainage device having a lower end with an adhesive composition thereon so that when the lower end is folded upon itself, the drainage opening is closed off, or, alternatively, the lower end is made of a material having intrinsic adhesive properties.

37 Claims, 11 Drawing Sheets

OSTOMY APPLIANCE AND WOUND DRAINAGE DEVICE WITH SELF ADHERING DRAIN SYSTEM

FIELD OF THE INVENTION

The present invention is directed to the field of ostomy appliances and wound drainage devices and particularly to an ostomy appliance and wound drainage device having a drain for the release of waste matter in which the draining system is formed at least in part by the employment of an adhesive composition.

BACKGROUND OF THE INVENTION

Ostomy appliances and wound drainage devices, hereinafter collectively referred to for brevity as ostomy appliances, generally include a bag or receptacle for collecting bodily wastes discharged from a surgically created stoma. The bag is connected to a substrate in the form of a pad or surgical dressing which is in contact with the patient's skin and surrounds the stoma.

The lower end of the ostomy appliance typically has an opening through which waste accumulated therein may be discharged. When the ostomy appliance is in use, the opening is closed off so that waste can be accumulated within the receptacle. When the appliance is full, the closure is removed and the waste can then be removed from the ostomy appliance. Thereafter the ostomy appliance can be cleaned and reused.

Various ways have been proposed for closing and then reopening the opening in an ostomy appliance. For example, L. Berger, U.S. Pat. No. 3,570,490 discloses folding the lower end of the appliance upon itself and then securing the fold by, for example, a clasp.

P. E. Riely, U.S. Pat. No. 3,690,320 discloses an ostomy appliance using a Velcro type of closure to fold one portion of the end upon itself to thereby close the opening.

M. C. Frank, U.S. Pat. No. 3,780,739 discloses the folding of the lower end of the ostomy appliance upon itself and securing the fold by means of tape, paper clips and the like.

L. J. Mattson, U.S. Pat. No. 4,233,977 discloses a closure for an ostomy appliance in which the lower end is folded upon itself and then secured by a semi-rigid strip affixed to one of the walls comprising the lower end of the appliance.

L. Fenton, U.S. Pat. No. 4,460,359 discloses a closure clamp made of a flexible plastic having a centrally located winding portion and a pair of closure wings. The wings may be folded to overlie the winding portion.

R. Schmidt, U.S. Pat. No. 4,790,833 employs a stopper to close off the opening in an ostomy appliance.

A. Ballan, U.S. Pat. No. 4,988,343 discloses a closing device including a reinforced plastic strip which is connected to the ostomy appliance.

K. L. Loveless, U.S. Pat. No. 5,022,693 discloses an ostomy appliance in which a removable clip assembly is used to close off the discharge opening when the ostomy appliance is collecting waste.

Closure devices of the type described above are disadvantageous because a) they require carefully articulated movements in order to close the opening, b) are expensive or cumbersome to produce, c) form an enlarged region in the closed position that can cause discomfort to the patient, d) are usually detectable and are therefore undesirable from the patient's perspective and/or e) do not always provide a continuous seal which can result in the emission of odors from residual waste fluids.

It would therefore be a significant advance in the art of producing ostomy appliances to provide a closure mechanism which can be readily and conveniently manipulated by the patient, is inexpensive to produce, provides a thin profile when the ostomy appliance is in the operable position for collecting waste and which substantially eliminates the problem of odors from residual waste.

SUMMARY OF THE INVENTION

The present invention is generally directed to an ostomy appliance having a thin-profile conveniently operated closure system whereby after waste is readily drained from an opening in the lower end of the appliance, the opening is closed by folding the lower end upon itself. At least the lower end portions of the appliance employ a releasable adhesive composition, preferably a washable adhesive composition, so that the folded ends adhere to each other to maintain the opening in the closed position in a thin, unobtrusive profile.

In particular, the present invention is directed to an ostomy appliance comprising:

a) a receptacle for storing waste material;
b) an opening in a lower end of the receptacle for releasing the waste material from the receptacle; and
c) adhesive means on the lower end of the receptacle enabling the lower end of the receptacle to be folded and releasably adhered to itself to thereby close off said opening.

In a preferred form of the invention, the adhesive can be cleaned by washing and the like. The adhesive means can be in the form of an adhesive layer applied to the lower end of the ostomy appliance or be a material used to form the lower end of the receptacle which itself has intrinsic adhesive properties (i.e. can be releasably secured to itself without the application of a separate adhesive layer).

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

The present invention is directed to an ostomy appliance and wound drainage device, collectively referred to herein for convenience as an ostomy appliance, in which the lower end thereof has an opening for enabling the waste material contained within the ostomy appliance to be drained. Once the waste material has been drained from the ostomy appliance, the lower end is folded upon itself and maintained in the folded condition by the application of an adhesive layer or by constructing the lower end from a material having intrinsic adhesive properties.

The adhesive layer is provided on the lower end of the ostomy appliance either on the outer or inner surface thereof as explained hereinafter. When the lower end is folded upon itself it is maintained in the folded position by a releasable adhesive bond which is sufficiently strong to maintain the lower end in the folded condition and thereby prevent leakage of the waste material from the ostomy appliance. When the ostomy appliance must be drained the lower end is pulled away from itself by breaking the releasable adhesive bond to allow waste material to expose the opening through which the waste material can flow out of the ostomy appliance. In a preferred from of the invention the adhesive is washable. Accordingly, the sealed area, upon breaking of the adhesive bond, can be cleaned by washing and the like.

As previously indicated, the lower end of the receptacle (e.g. a tube) can be constructed of a material having intrinsic adhesive properties. As used herein the term "intrinsic adhesive properties" shall mean that the material can stick to itself when folded over without the application of a separate adhesive layer.

Figure 1:
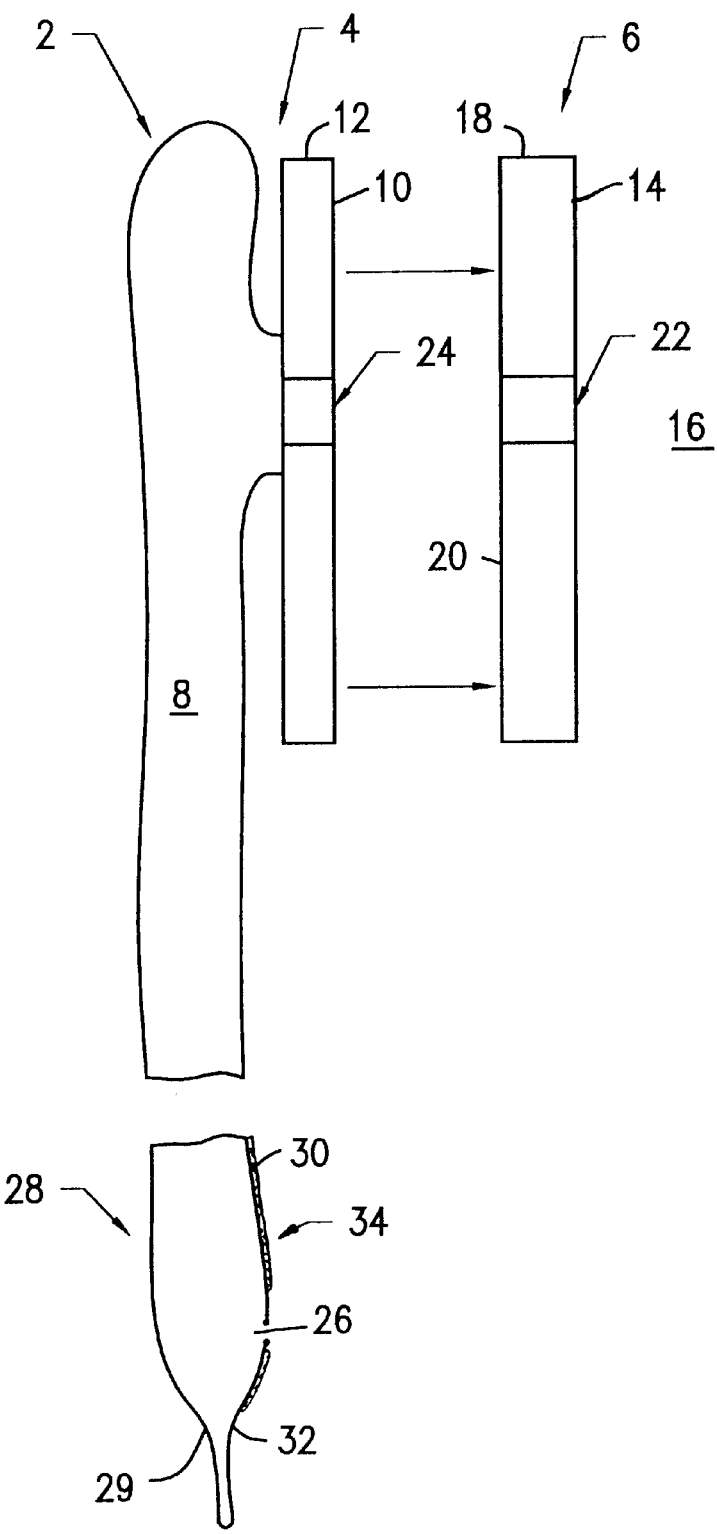
FIG. 1 is a side elevational view of an ostomy appliance in accordance with the present invention having an adhesive layer on the lower end thereof.

Referring to the drawings and first to FIG. 1, there is shown an ostomy appliance 2 having two components 4, 6 capable of being coupled together in a fluid tight relationship. The first of these components is a receptacle side component 4 and the second component is a body side component 6. The receptacle side component 4 includes a receptacle 8 for collecting discharged waste (liquids and/or gases) from the patient. As used herein the term "receptacle" shall include bags, pouches and the like which can be employed to collect waste fluids from an ostomy patient.

The receptacle side component 4 includes some means such as an adhesive layer 10 connected to the receptacle 8 through a substrate 12 which provides support for the adhesive layer 10 to enable the two components 4,6 to be coupled together during operation. The substrate 12 can be made from any material which provides a surface for placement of the adhesive. Preferred substrates are webs or films, preferably having an irregular surface (e.g. naps) to ensure anchoring of the adhesive layer 10 thereto. Examples of such substrates include non-woven fabrics made of polypropylenes, polyethylenes, polyesters, rayons and the like including blends thereof.

The body side component 6 of the ostomy appliance 2 includes a body side adhesive layer 14 which is adapted to adhere to the patient's skin and is shown generally by the numeral 16. Adhesive compositions which can be used to adhere the ostomy appliance 2 to the patient are known and include those described in U.S. Pat. Nos. 4,253,460; 4,393,080 and 4,551,490, each of which is incorporated herein by reference.

Figure 2:
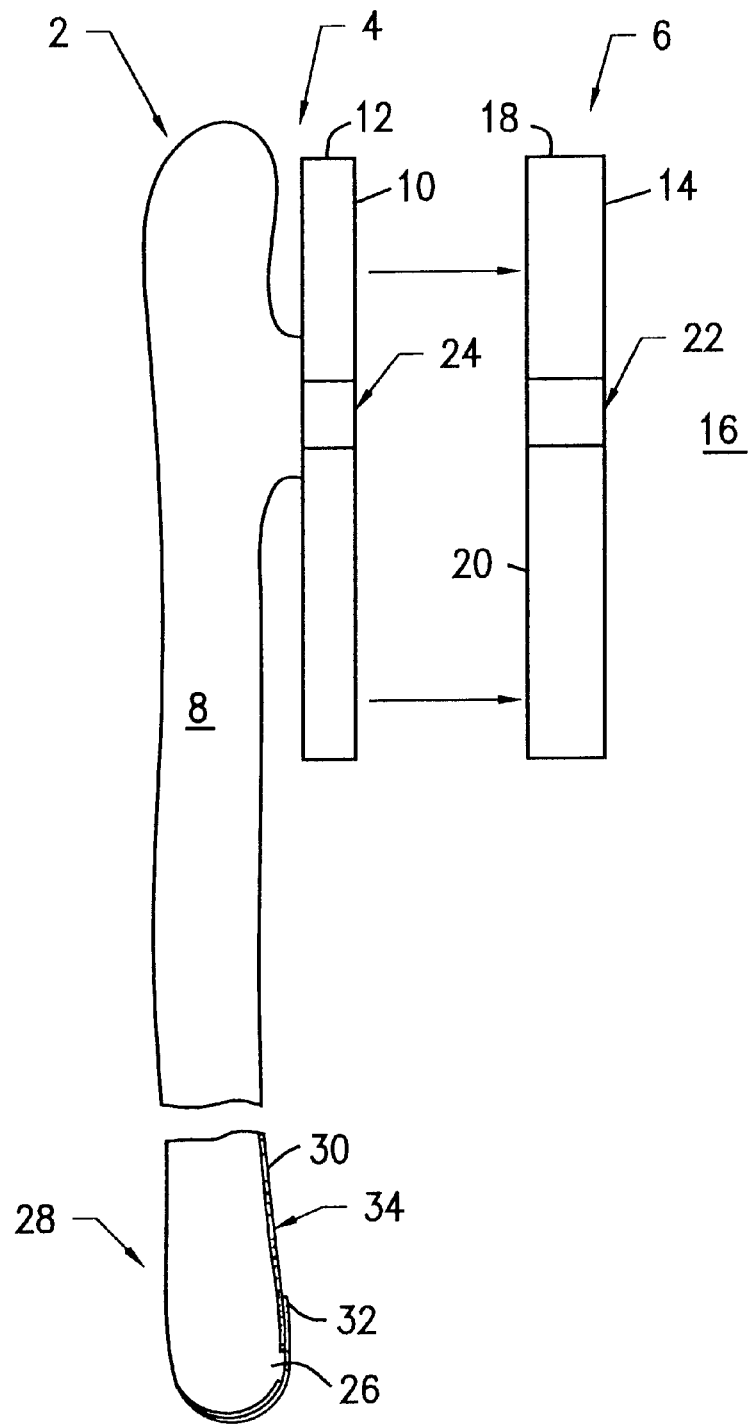
FIG. 2 is a side elevational view of an ostomy appliance, similar to FIG. 1 showing the lower end of the ostomy appliance folded and releasably adhered to itself.

As shown in the embodiment of FIGS. 1 and 2, the body side component 6 is further provided with a substrate 18 and an adhesive layer 20 which correspond in structure and function to the substrate 12 and the adhesive layer 10, respectively of the receptacle side component 4.

Each of the components 4,6 is provided with a passageway 22, 24, respectively to enable waste fluids from the patient to travel into the receptacle 8. The receptacle 8 is provided with an opening 26 positioned at or towards the end point 29 of the lower end 28 of the ostomy appliance 2. In the specific embodiment shown in FIG. 1, the opening 26 is positioned towards but spaced apart from the end point 29. When the receptacle is in an extended position as shown in FIG. 1, waste contained within the receptacle can flow out of the opening 26 enabling the receptacle 8 to be drained and optionally cleaned and sterilized for reuse. When the receptacle 8 is attached to the patient and is in position to collect waste received through the passageways 22, 24, the opening 26 must be closed to prevent waste from flowing therethrough.

In accordance with the present invention, the lower end 28 of the receptacle 8 is provided with an adhesive layer 30, preferably a washable adhesive, shown on the outer surface of the lower end 28 of the receptacle 8 from a region 32 below the opening 26 to a region 34 located above the opening 26. It is preferred that the length of the adhesive layer 30 be limited so that the adhesive does not interfere with a patient's clothing.

In accordance with the present invention, when the region 32 is folded upwardly and over so that it contacts the region 34, the adhesive layer 30 of the respective regions 32, 34 adhere to each other thereby closing the opening 26 to prevent the flow of waste from the receptacle 8. Referring to FIG. 2, the ostomy appliance 2 is shown with the bottom region 32 folded upwardly so that it contacts the region 34 lying above the opening 26. The regions 32, 34 adhere to each other in a manner that releasably secures the region 32 to the region 34 thereby closing off the opening 26 because each region has thereon the adhesive composition.

As shown in FIGS. 1 and 2, the closing of the opening 26 is readily accomplished by the patient by merely grabbing the lower end 28 of the receptacle 8 in the region 32 and folding the same upwardly and over. This is a marked improvement over typical valve-like mechanisms that require dexterity and careful manipulation to close off the opening. This further presents an improvement over devices employing hook and eye closures (e.g. material sold under the trademark Velcro) which are more difficult to manufacture and can be more expensive to produce. In addition, the profile of the ostomy appliance when the opening is closed off is considerably thinner than appliances employing valves or add-on materials such as hook and eye closures.

Figure 3:
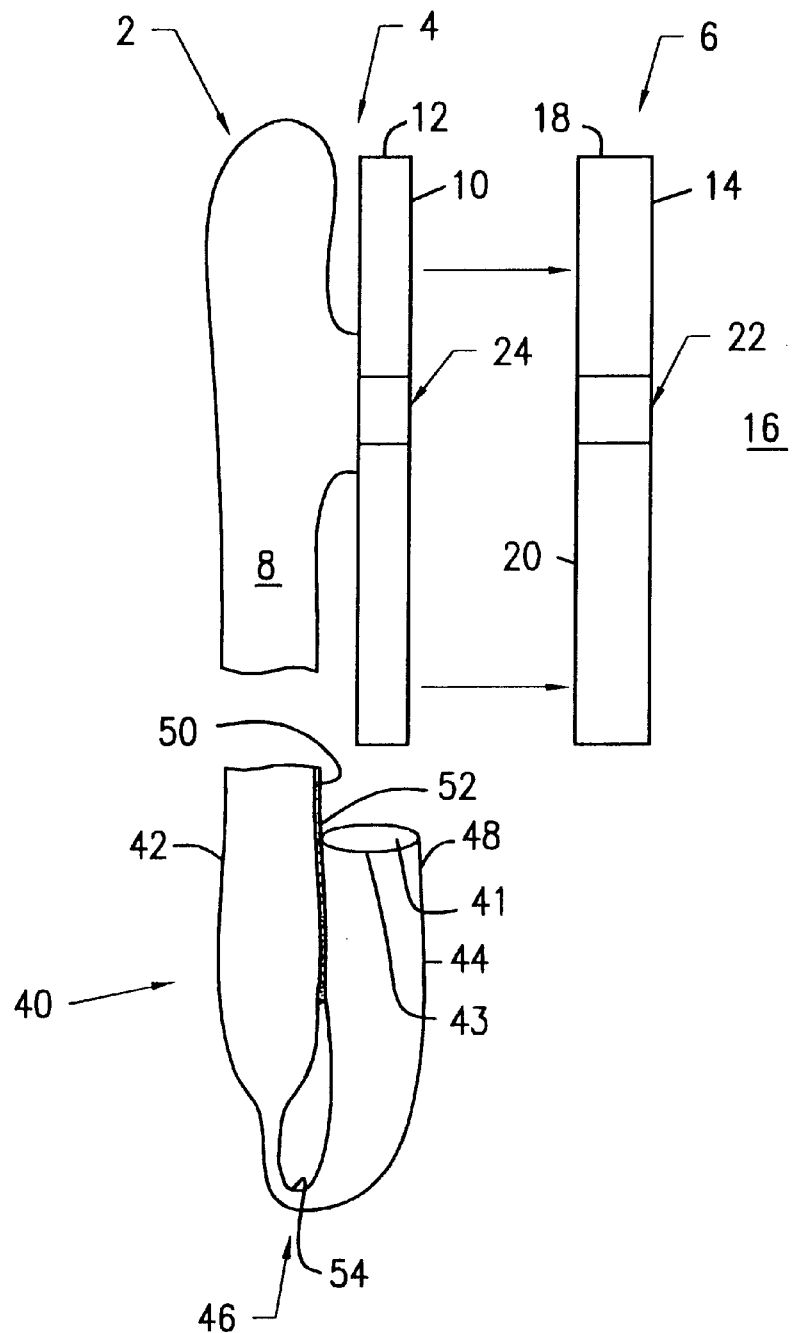
FIG. 3 is a side elevational view of an ostomy appliance with a drainage tube folded upon itself employing an adhesive on the exterior surface of the tube.
Figure 4:
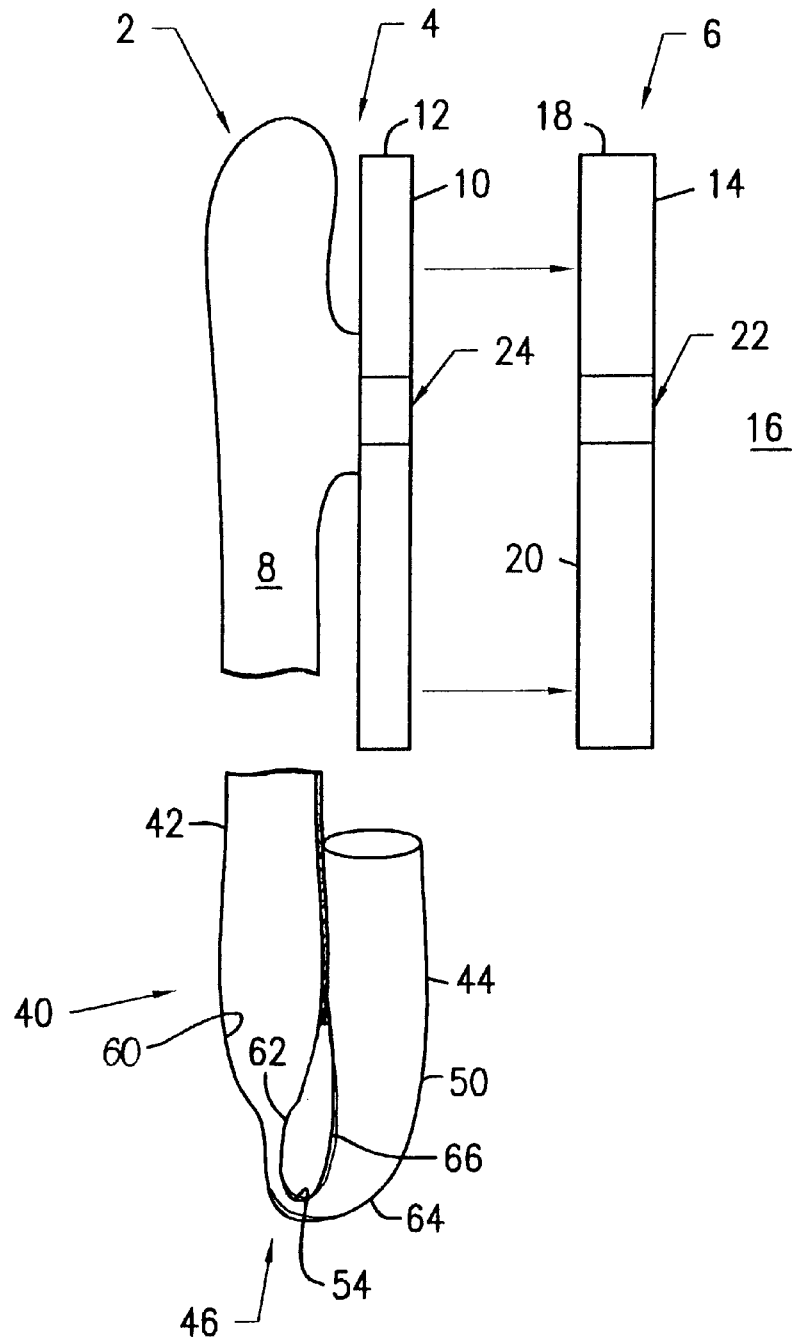
FIG. 4 is a side elevational view similar to FIG. 3 with an adhesive on the interior surface of the tube.

Other embodiments of the invention are shown in FIGS. 3 and 4. Referring to FIG. 3 there is shown an ostomy appliance 2 having a drainage tube 40 with an opening 41 at the end point 43 for discharging waste material. The tube 40 when fully extended allows liquid and/or gaseous waste material to pass out of the ostomy appliance from the receptacle 8. The tube 40 has an upper end 42 and a lower end 44 separated by a central region 46 about which the tube 40 can be bent. The outer surface 48 of the lower end 44 and/or the outer surface 50 of the upper end 42 is provided with an adhesive layer 52 (shown only on the outer surface 50 for convenience). The adhesive layer 50 enables the lower end 44 to adhere to the upper end 42 so as to remain in the position shown in FIG. 3. As a consequence, a bend 54 is maintained in the central region 46 which narrows the diameter of the tube 40 to the extent that fluid cannot pas therethrough. The tube can also be manufactured from material that has intrinsic adhesive properties and is preferably washable. The tube can therefore adhere to itself when a bend is made.

In operation, the patient attaches the ostomy appliance 2 to the skin 16 about the stoma. The tube 40 is folded over and maintained in the folded-over position shown in FIG. 3 by releasably affixing the lower end 44 of the tube 40 to the upper end 42 through the adhesive layer 50 position on the outer surface 50 of the lower end 42 and/or the upper end 44. When the receptacle 8 needs to be drained, the patient grips the lower end 44 of the tube 40 and pulls it away from the upper end 42 to thereby disengage the two so that the tube 40 may extend downwardly thereby eliminating the bend 54 and allowing the contents of the receptacle to flow through and out of the tube 40 through the opening 41 at the end point 43.

In a further embodiment of the invention, the adhesive can be applied to the inner surface of the tube in the central region 46. When the tube is bent by the patient as described above in connection with FIG. 3, the opposed walls of the inner surface of the tube releasably adhere to each other so that the tube remains in the folded-over condition during operation of the ostomy appliance.

Referring to FIG. 4, there is shown an ostomy appliance 2 having a tube 40 with an inner surface designated by numeral 60. The inner surface comprises opposed walls shown by numerals 62 and 64 in the central region 46 of the tube 40. The inner surface 60 in its entirety, or at least one of the opposed walls 62 or 64, is provided with an adhesive layer 66 thereon. As specifically shown in FIG. 4, the entire inner surface 60 of the tube 40 in the central region 46 is provided with the adhesive layer 66. As with the embodiment described in FIG. 3, the tube 40 may be made of a material which has an intrinsic adhesive properties and is preferably washable.

In operation, the drainage of the ostomy appliance 2 in the embodiment of FIG. 4 is accomplished as described in connection with the embodiment of FIG. 3. The lower end 44 of the tube 40 remains in releasable engagement to the upper end 42 by the adhesive bond formed at the central region 46. When the ostomy appliance is ready to be drained, the patient pulls the lower end 44 away from the upper end 42 to release the adhesive bond to thereby enable the contents of the receptacle 8 to drain therefrom. When a washable adhesive is employed the adhesive may then be washed before reusing the ostomy appliance.

Figure 5A:
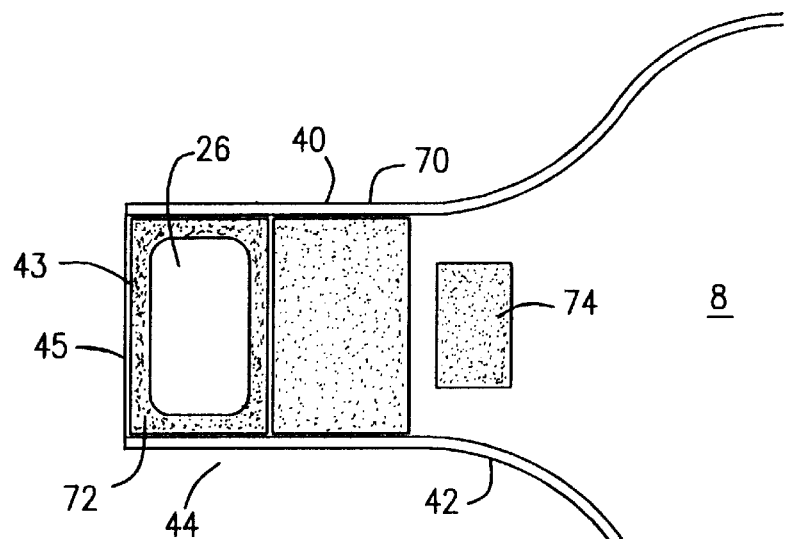
FIG. 5A is a partial plan view of the lower portion of an ostomy appliance of another embodiment of the present invention.
Figure 5B:
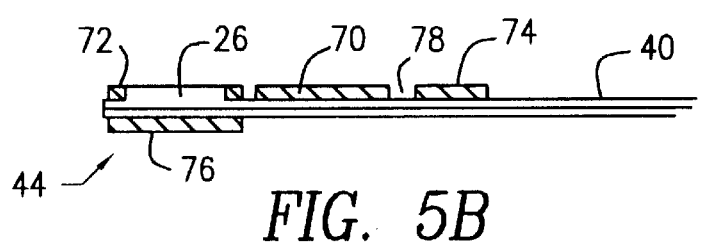
FIGS. 5B–5C are respective side views of the embodiment shown in FIG. 5A showing the stepwise closure of the lower end of the ostomy appliance.

A further embodiment of the invention is shown in FIGS. 5A–5D. In this embodiment of the invention the lower end of the tube of the ostomy appliance is provided with three adhesive areas on the outside of one side the tube and a separate adhesive area on an opposed side of the tube. Referring specifically to FIG. 5A, the tube 40 has an opening 26 at the lower end 44 thereof. Surrounding the opening 26 is an adhesive area 72. Immediately above the adhesive area 72 (i.e. toward the receptacle 8) is a further adhesive area 70 and a third adhesive area 74 above and spaced apart from the adhesive area 70. On the opposed side of the tube as best shown in FIG. 5B is an adhesive area 76 which will serve to finally secure the tube 40 in the folded up position as described hereinafter.

Figure 5C:
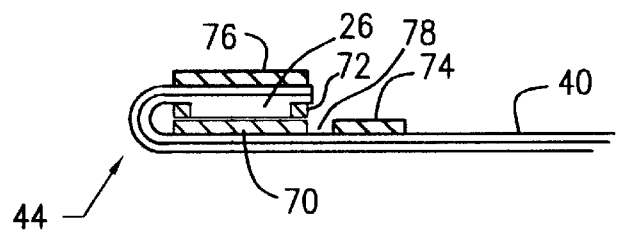
Figure 5D:
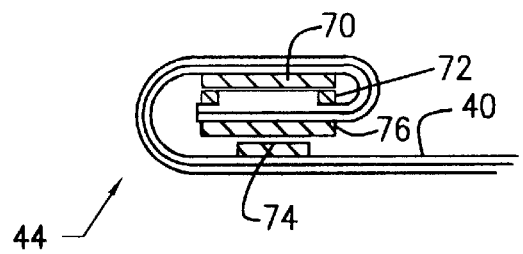

Referring sequentially to FIGS. 5B–5D, FIG. 5B shows in side view the positioning of the respective adhesive layers 70, 72, 74 and 76. In the position shown in FIG. 5B, liquid and gaseous waste from the receptacle 8 is allowed to pass through the opening 26 so that it can be evacuated from the ostomy appliance 2. After evacuation, the ostomy appliance 2 can be placed in the fluid storing position with the lower end 44 of the tube 40 folded upon itself so that fluid cannot pass through the opening 26.

Referring to FIG. 5C, the tube 40 is folded over upon itself at lower end 44 to assume the position shown specifically in FIG. 5C. In this position, the adhesive area 72 releasably adheres to adhesive area 70 thereby closing off the flow of liquid and gaseous waste material through the opening 26 effectively sealing the receptacle. The adhesive bond between the adhesive areas 70 and 72 can be sufficient to close the opening 26 while the ostomy appliance is in use.

Further security for ensuring that the lower end 44 of the ostomy appliance 2 is closed off to fluid flow is shown in FIG. 5D. In this regard, the adhesive areas 72 and 70 shown in FIG. 5C are further folded so that the adhesive area 76 is releasably secured to the adhesive area 74. There is a space between the adhesive areas 70 and 74 designated by the numeral 78. The width of the space is sufficient to enable the second fold over procedure shown in FIG. 5D to be performed. Alternatively, as explained in detail in connection with FIG. 12, score lines may be used to enable the folding over of the tube upon itself.

In a preferred form of the invention shown in FIGS. 5A–5D, the adhesive area 72 surrounding the opening 26 can be reinforced with a thick backing material, typically made from semi rigid polyethylene, ethylene vinyl acetate or similar materials. The thick backing material provides better leverage when the adhesive area 72 is folded upon adhesive area 70 therefore ensuring a uniform seal with the adhesive area 70. The thick backing material can be coextruded with the adhesive or laminated thereon in a conventional manner.

Figure 6A:
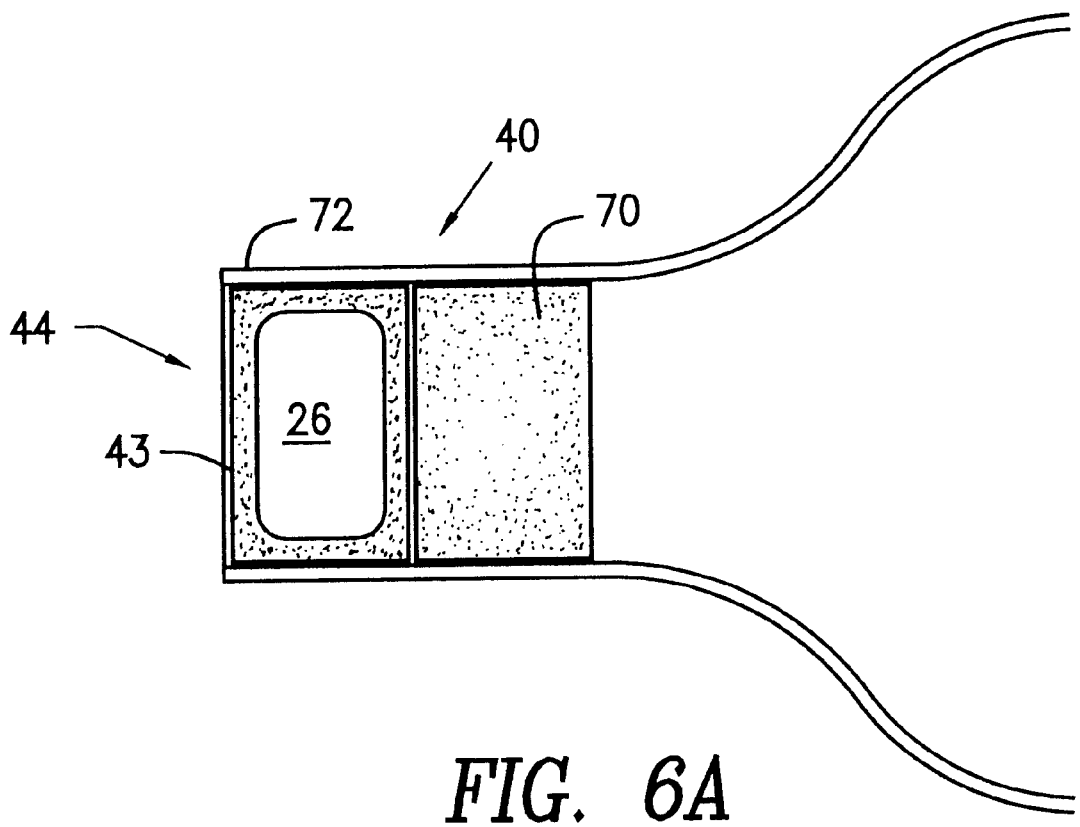
FIG. 6A is a partial plan view of a further embodiment of the present invention.
Figure 6B:
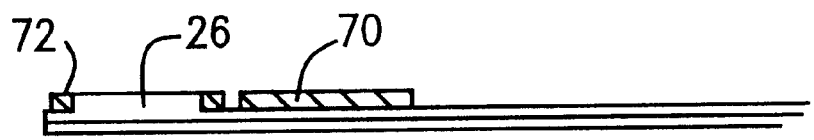
FIG. 6B is a side view of the embodiment shown in FIG. 6A.
Figure 6C:
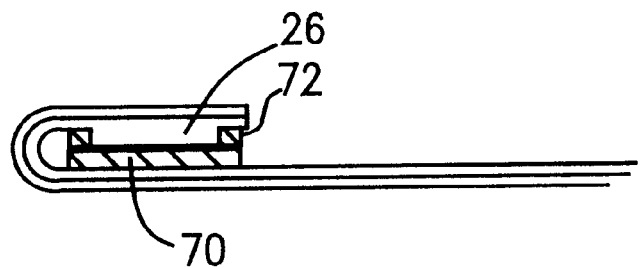
FIG. 6C is a side view of the lower end of the ostomy appliance shown in FIG. 6A in a closed position for retaining fluid therein.

In another embodiment of the present invention as shown in FIGS. 6A–6C, the adhesive area 74 is eliminated so that the adhesive areas 72 and 70 provide the sole means of securing the lower end 44 of the adhesive appliance 2 in a position to close off the opening 26. As with the embodiment shown in FIGS. 5A–5D, it is preferred for the adhesive area 72 to have a relatively stiff backing material to provide greater leverage to assist in securing of the adhesive area 72 to the adhesive area 70.

In the embodiments shown in FIGS. 5A–5D and FIGS. 6A–6C, the opening 26 is positioned spaced apart from the end point 43. Positioning of the opening 26 spaced apart from the end point 43 ensures that the end point 43 is free of waste material debris. This is because the end point 43 can be sealed along a seal line 45 as shown in FIGS. 5A and 6A.

In the embodiments represented by 5A and 6A, there are times when waste material can become retained in the area of the opening 26, particularly between the edge of the opening 26 and the end point 43. While effort can be made to remove such residual waste material, any waste material which is left over can result in offensive odors which requires recleaning of the ostomy appliance, sometime before the receptacle 8 is filled with additional waste material.

Figure 7A:
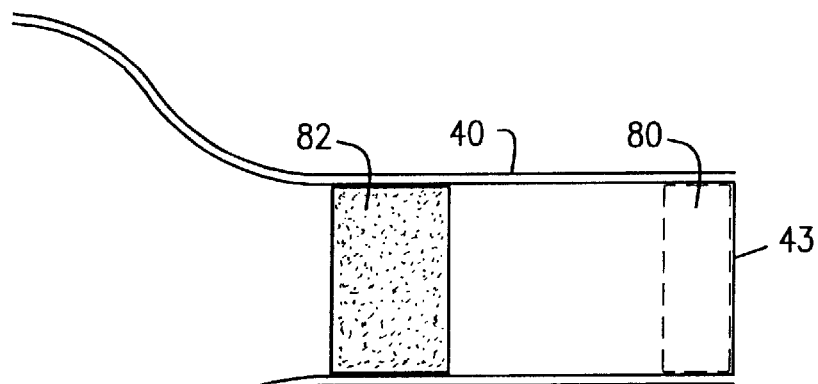
FIG. 7A is a partial plan view of a still further embodiment of the present invention.
Figure 7B:
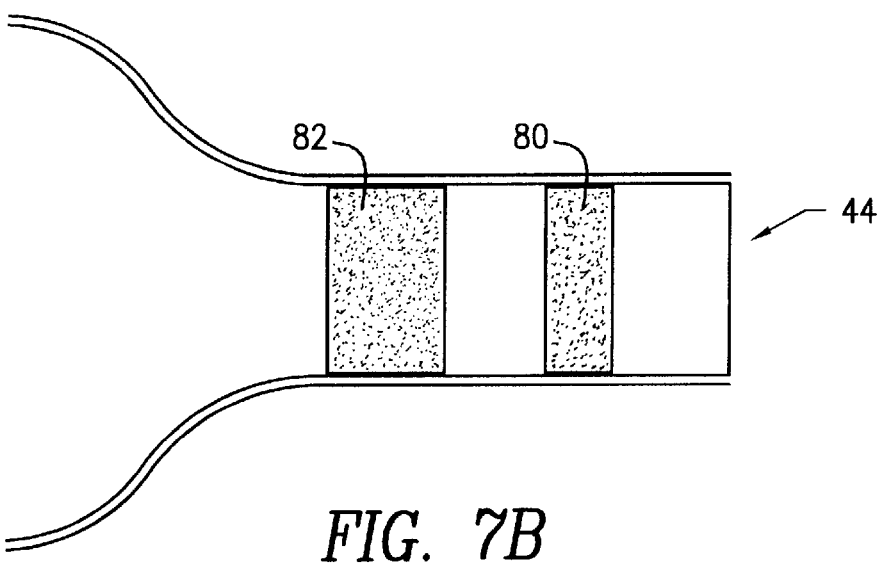
FIG. 7B is a partial plan view similar to FIG. 7A showing the end of the ostomy appliance folded upon itself.
Figure 7C:
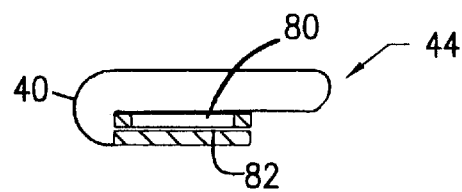
FIG. 7C is a side view of the lower end of the ostomy appliance of FIG. 7A in the closed position for retaining fluid therein.

In another embodiment of the invention, the opening is placed at the end point which makes it easier to remove residual waste material before reusing the ostomy bag. Such an embodiment is shown in FIGS. 7A–7C. Referring to FIG. 7A, the opening of the tube (not shown) is placed at the end point 43. At the end point 43 there is provided a first adhesive area 80 which is placed on the underside of the tube 40. Spaced apart from the adhesive area 80 is a second adhesive area 82 which is placed on the opposite side of the tube 40.

As shown in FIG. 7B, the lower end of the tube 44 is folded upon itself so that the first adhesive area 80 now appears on the same side as the adhesive area 82 of the tube 40. The lower end 44 of the tube 40 is then folded again upon itself so that the adhesive areas 80 and 82 contact each other as shown in FIG. 7C to form a releasable seal. The formation of the releasable seal prevents liquid and gaseous waste material from exiting the opening at the end point 43 of the tube 40.

Figure 8A:
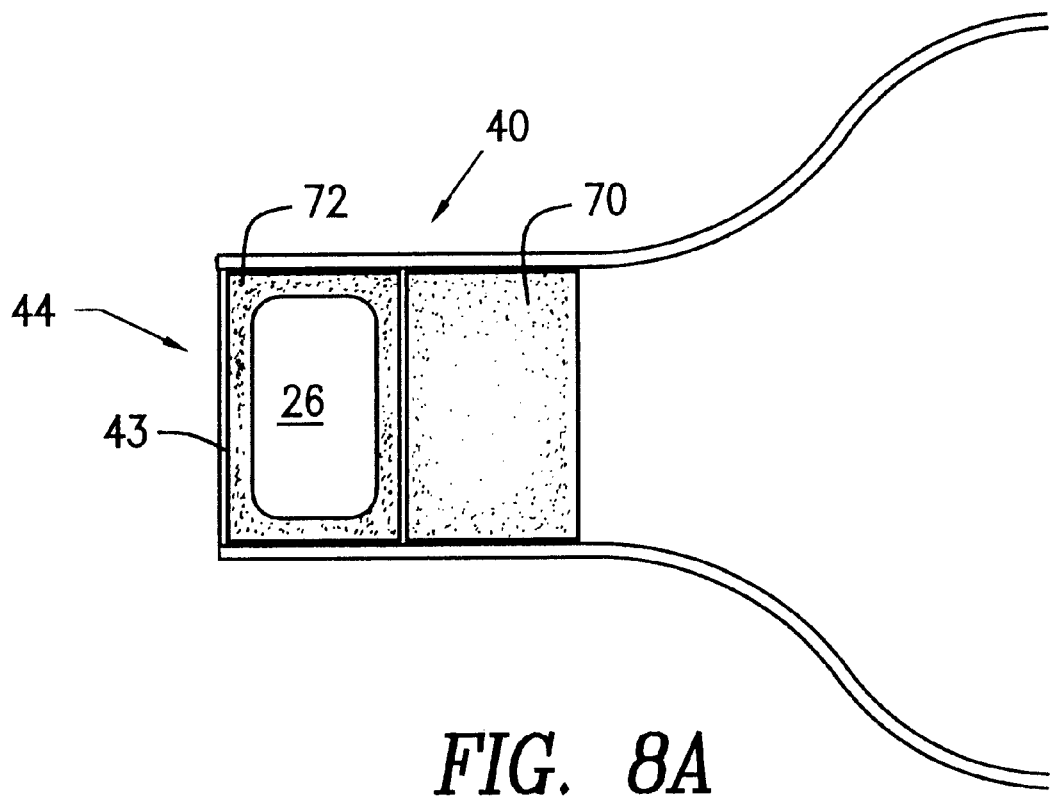
FIG. 8A is a plan view of a further embodiment of the invention.
Figure 8B:
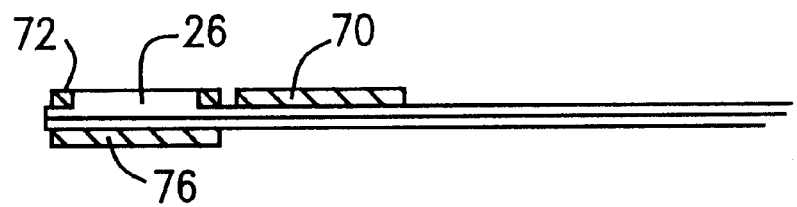
FIG. 8B is a side view of the embodiment shown in FIG. 8A.
Figure 8C:
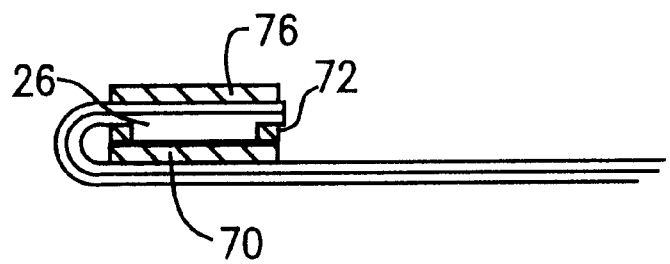
FIG. 8C is a side view of the lower end of the ostomy appliance of FIG. 8A in a closed position for retaining fluid therein.

In a still further embodiment of the invention as shown in FIGS. 8A–8C, the adhesive areas 70 and 72 are combined with an adhesive area 76 located on the opposite side of the tube 40 as shown specifically in FIG. 8C. The lower end 44 of the tube 40 is folded over so that the adhesive layer 72 forms an adhesive seal with the adhesive layer 70 thereby closing off the opening 26. As a further measure of protection, the tube 40 is folded over once again upon itself so that the adhesive layer 76 forms an adhesive seal with the surface of the tube 40.

Figure 9:
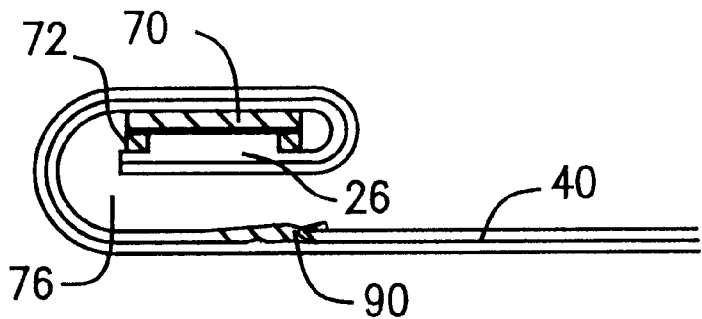
FIG. 9 is a side view of another embodiment of the invention similar to the embodiment of FIGS. 8A–8C except that the tube itself is made of an adhesive for sealing the lower end of the tube in the closed position.

In an embodiment related to FIGS. 8A–8D the adhesive layer 76 can be omitted and in its place the tube 40 can itself be made of an adhesive material. As specifically shown in FIG. 9, the adhesive layer 76 (shown in FIGS. 8A–8D) is eliminated and instead the tube 40 has a region 90 which is made of an adhesive material which can adhere to the folded over end of the ostomy appliance.

Figure 10A:
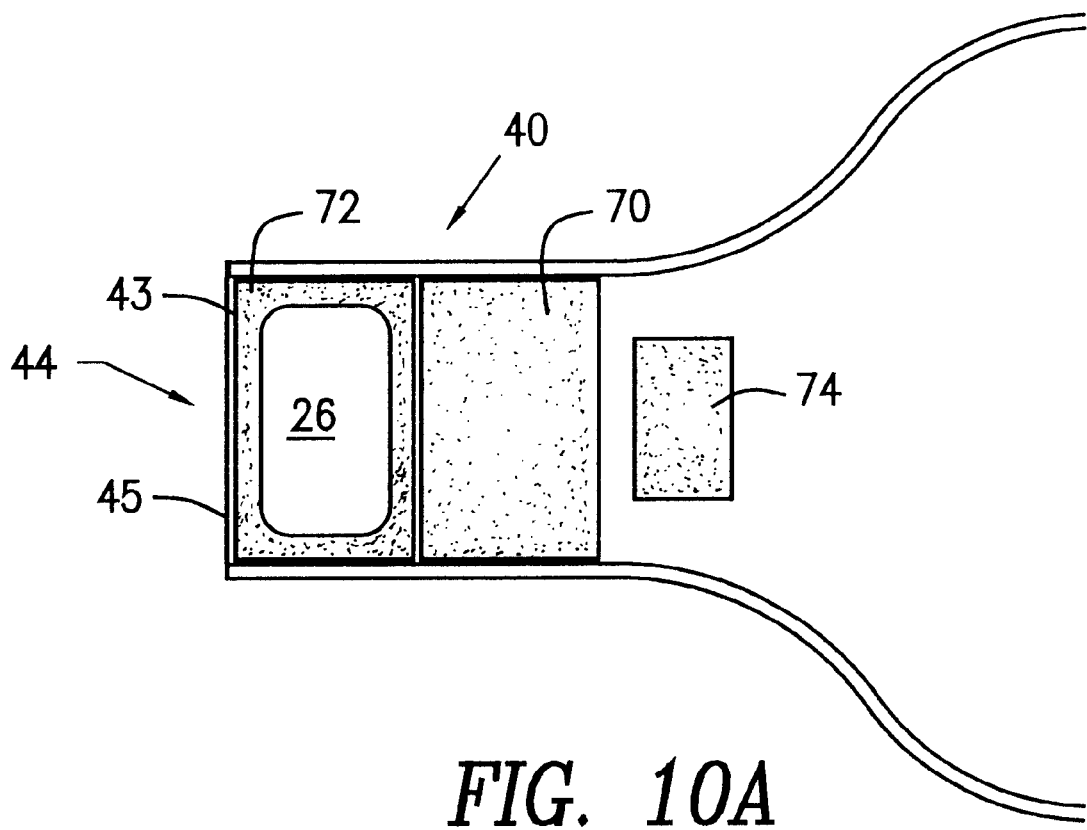
FIG. 10A is a plan view of a still further embodiment of the invention.
Figure 10B:
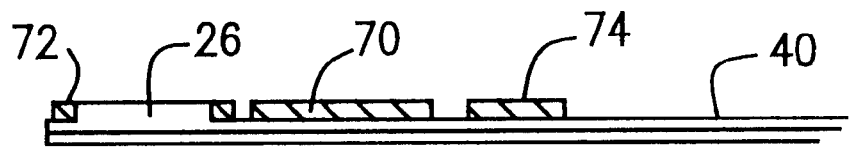
FIGS. 10B–10D are side views of the embodiment shown in FIG. 10A as the lower section is moved toward the closed position.
Figure 10C:
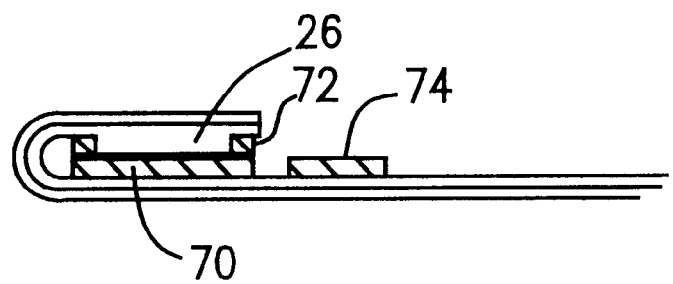
Figure 10D:
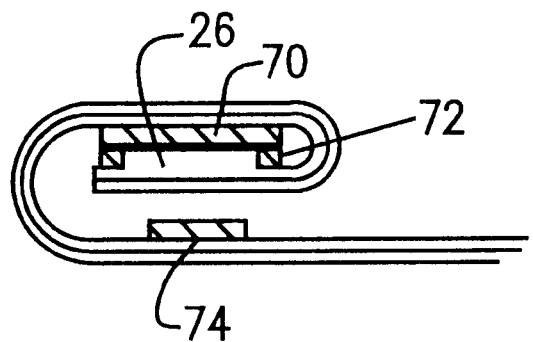

In a still further embodiment of the invention, all of the adhesive layers can be situated on the same side of the tube. As shown in FIG. 10A, three adhesive layers 70, 72 and 74 are provided on the same side of the tube 40. As with some of the previous embodiments, the end point 43 is sealed along a line 45. As shown best in FIGS. 10C and 10D, the lower end 44 of the tube 40 is folded upon itself so that the adhesive layer 72 is secured to the adhesive layer 70 thereby closing off the opening 26. Further protection is provided by folding the lower end 44 of the tube over upon itself again so that the underside of the tube 40 is placed into contact with the third adhesive layer 74 as shown best in FIG. 10D.

Figure 11A:
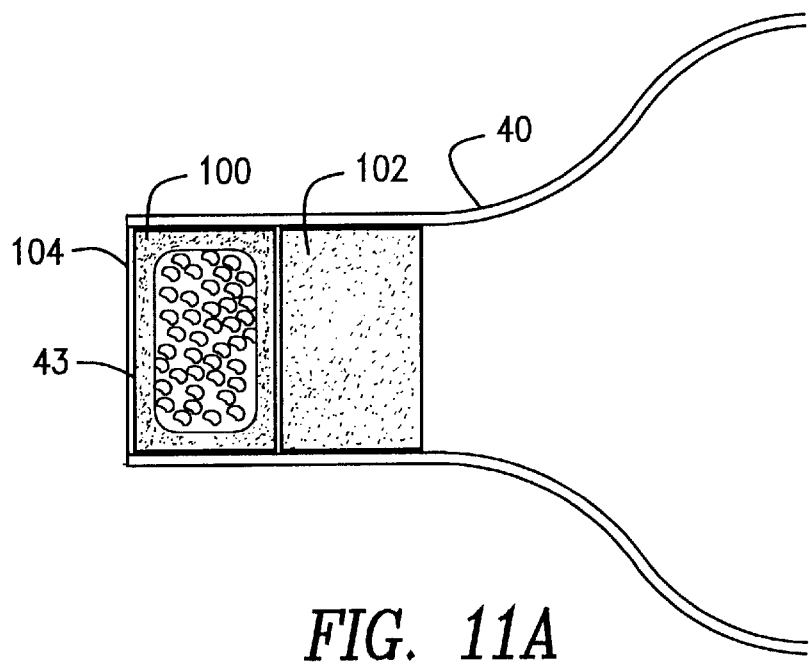
FIGS. 11A is a plan view of a still further embodiment of the invention.
Figure 11B:
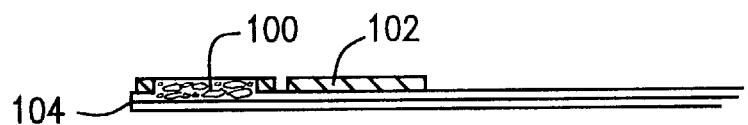
FIG. 11B is a side view of the embodiment shown in FIG. 11A.
Figure 11C:
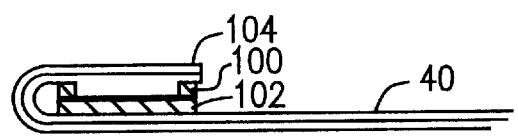
FIG. 11C is a side view of the embodiment shown in FIG. 11A in the folded over position.

The present invention is also applicable to ostomy appliances wherein the lower end of the tube is not sealed but has an opening allowing waste products to be drained therefrom. Referring to FIGS. 11A and 11B, there is shown an embodiment of an ostomy appliance in accordance with the present invention in the form of a tube 40 having two adhesive layers 100 and 102. The end point 43 of the tube is not sealed and thereby provides an opening 104 through which waste product can flow if the tube is in the position shown in FIG. 1A. As shown in FIG. 11C, the end of the tube can be folded upon itself so that the adhesive layer 100 contacts the adhesive layer 102 to form a seal thereby closing off the flow of fluid through the opening 104.

The employment of an open end 104 as shown in FIG. 11A can be applied to ostomy appliances having the same configurations as shown in FIGS. 5–10. The position of the various adhesive layers shown in FIGS. 5–10 is duplicated with the exception of the adhesive layer 72 which no longer surrounds an opening 26. Instead there is provided an adhesive layer 100 which covers the entire width of the tube 40.

In the embodiments described in connection with FIGS. 5–11, the various adhesive layers lying on the same side of the tube were spaced apart. For example, as shown in FIG. 5C, there is a space designated by the numeral 78 between the adhesive areas 70 and 74. The width of the space is sufficient to enable the second foldover procedure shown in FIG. 5D to be performed. Thus, the spaces between the adhesive layers are provided to enable the end of the tube to be folded upon itself so that the various adhesive layers may be provided with optimum face to face contact to releasably secure the layers to each other. In these embodiments, it is necessary to apply separate adhesive layers separated by the spaces previously described. However, in another preferred embodiment of the invention, the space between the adhesive layers may be eliminated as more fully described below in connection with FIG. 12.

Figure 12:
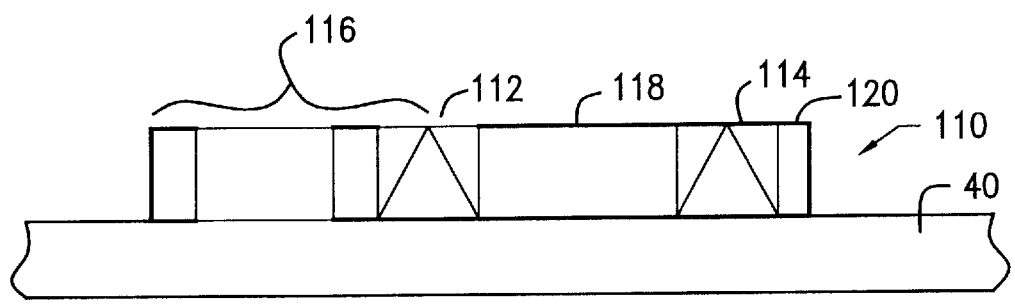
FIG. 12 is an embodiment of the invention shown in FIGS. 5A–5D with a scoreline separating each pair of adjacent adhesive areas.

As shown in FIG. 12, there is shown an adhesive layer 110 placed on a surface of the tube 40. The adhesive layer 110 shown specifically in FIG. 12 has two scorelines 112 and 114 which partially separate the adhesive layer 110 into respective adhesive regions 116, 118 and 120. The adhesive region 116 is shown surrounding an opening 26 and thus the configuration shown in FIG. 12 is similar to that shown in FIG. 10B except that scorelines 112 and 114 are used to differentiate areas of the adhesive as opposed to spaces. The advantage of employing scorelines 112 and 114 is that the adhesive layer 110 can be applied to the tube 40 in a single operation.

It will be understood that scorelines can be used in any of the embodiments shown in FIGS. 5–11 wherein a space is required between adjacent regions of adhesive so that the tube can be folded upon itself.

In accordance with the aforementioned embodiments of the invention, the formation of the releasable seal by turning the tube upon itself provides distinct advantages over prior art devices in which the final position of the lower end of the tube is maintained by clips, hook and eye fasteners and other mechanical fastening devices. The present invention provides a more sleek profile so that the ostomy appliance remains inconspicuous when in use by a patient. In addition, the formation of the final releasable seal can be readily achieved by most patients even those suffering from conditions which adversely affect manual dexterity.

It will be understood that the embodiments of the present invention as exemplified by FIGS. 1–12 may be used in conjunction with well-known devices for maintaining the ostomy appliance in the fluid-storing position. Such devices as clips, tape and the like may be employed to provide additional means for maintaining the drainage tube or opening in the fluid-storing position.

The adhesives which are used to form the adhesive layers and/or adhesive regions of the tube itself, include thermoplastic elastomers such as styrene copolymers and acrylic adhesives. The preferred styrene copolymers include styrene-acrylonitrile-butadiene, styrene-butadiene-styrene, styrene-isoprene-styrene, styrene-ethylene/butylene-styrene and the like and blends thereof. Such copolymers of styrene are available, for example from Shell Chemical Company under the trademark Kraton. A preferred styrene copolymer is styrene-isoprene-styrene copolymer (e.g. Kraton D 1107 from Shell Chemical Company). Another preferred copolymer is styrene-acrylonitrile-butadiene having a relatively high butadiene content.

A preferred adhesive is one which may be washed and reused. Washable adhesives of this type include a gelled "Kraton" adhesive (e.g. Kraton D 1107) in which the styrene based polymer is gelled with an oil, preferably mineral oil. The amount of the styrene based polymer is preferably from about 70 to 90% by weight and the amount of the mineral oil is from about 10 to 30% by weight, based on the total weight of the styrene based polymer.

The adhesive composition of the type described above may be prepared, for example, by heating the mineral oil to a temperature of from about 120 to 150° C. and then adding the copolymer (e.g. Kraton D 1107) under stirring until the copolymer is dissolved. The resulting adhesive composition can be poured onto a suitable substrate or applied by a common hot melt applicator.

The most preferred types of adhesives are those which can be washed by conventional cleaning implements such as tissues and cloths without retaining fibers thereon and which form a fluid tight seal even after many applications. Such adhesives are disclosed, for example, in Homer C. Amos et al., U.S. Pat. No. 3,682,690, incorporated herein by reference.

In particular, the most preferred adhesive compositions are comprised of an elastomeric composition having a modulus of elasticity sufficient to enable waste particles to be readily removed therefrom with an internal viscosity low enough to enable water-washing and high enough to provide tack. Preferably the modulus of elasticity is in the range of from about 1 to 100 psi and the internal viscosity is from about 1,000 to 20,000 poises. Preferred adhesive compositions are made of high molecular weight polyvinyl chloride or copolymers of vinyl chloride and vinyl acetate.

For water-washing applications as desired for the present ostomy appliance, the adhesive composition is hydrophobic wherein water will readily run off the surface, leaving the surface dry.

The softness of the tacky material used in the preferred adhesive composition can range from a modulus as low as 1, at which point the material is weak, to a modulus as high as 100. Values in the upper part of the range are satisfactory only with materials with a high "intrinsic adhesivity", i.e., a high surface free energy. In general, the softer, i.e., the lower the modulus, the greater the tack. Some materials, such as some polyvinyl chloride compositions, have a quite non-linear stress-strain curve. The first portion of the curve shows a very low modulus, but later the curve becomes very steep, indicating a very high modulus. In such materials, one can get the benefit of great softness with relatively high toughness.

Another requirement for washable tackiness which is particularly significant, is an internal viscosity between about 1,000 and 20,000 poises.

Most elastomers require a plasticizer to achieve a modulus as low as is desired. Materials such as neoprene and high-molecular-weight vinyls have little internal viscosity of their own, and the viscosity of the plasticized material is a fairly accurate reflection of the viscosity of the plasticizer itself. In any event, the internal viscosity must be low enough so that the material can quickly flow into large surface contact with the surface of the object to which tack is sought. But the viscosity must also be high enough so that the material does not yield too quickly to any force seeking to remove the object tacked onto the adhesive. Too low a viscosity results in little apparent tack. On the other hand, too high a viscosity results in the material feeling tacky with sustained contact pressure but not flowing quickly enough into large surface contact, with the contact surface, which involve very short-time contact pressure. Experience has shown that a viscosity in the neighborhood of 2,500 to 5,000 poises is most preferred. In general, viscosities outside the range of from 1,000 to 20,000 poises give inferior results.

The internal viscosity can be measured by conventional means. In the case of highly plasticized vinyls or neoprene, measurement is unnecessary, for the plasticizer used therewith determines the resultant viscosity. The internal viscosity of materials such as polysulfides or polyurethanes which do not employ a plasticizer can be determined by comparing them with materials whose viscosity is known from its plasticizer.

A ball or the material in question is prepared, and a similar ball is prepared of the same modulus in a mixture of a high-molecular weight polyvinyl chloride, such as Geon 121 (sold by the Geon Company of Cleveland, Ohio) with a plasticizer whose internal viscosity is known. The surfaces are dusted with talc or a similar powder, and the rebounds are compared, the greater the rebound, the lower the viscosity. This method is crude but effective so long as care is taken to make the modulus, an easily measured property, of the two balls equal. A better method is that described in detail in U.S. Pat. No. 3,682,690.

Tack is the result of a particular degree of softness and internal viscosity in combination with a property which might be termed the "intrinsic adhesivity", but which is better known as "surface free energy", the degree to which the Van der Waals forces within the material are bound. For example, in materials such as waxes or polytetrafluoroethylene, or materials generally composed of long unbranched chain molecules, the molecular bonds are tightly bound and show little of this quasi-chemical activity at the surface. Such materials can be described as having a low intrinsic adhesivity. On the other hand, materials composed of short chain or highly branched molecules have many chain ends on any given surface, and thus have a high degree of quasi-chemical activity at the surface. Such material can be described as having a high intrinsic adhesivity. When compounding or choosing a washable tacky elastomer for a given application, the proper choice of characteristics as taught herein can be used to a great advantage. For instance, when extreme ease of washability is desired, a material such as a very high molecular weight polyvinyl chloride can be used as a base resin. High washability is obtained when materials have a low surface free energy and high elasticity. The application of the principles taught herein regarding modulus and internal viscosity will give an aggressive tack even though the base resin has a low intrinsic adhesivity, by the addition of a suitable plasticizer.

If a plasticizer is used, it is important that it be highly compatible and not subject to excessive "sweating". It is preferred that the plasticizer be highly resistant to extraction by soapy water, since, otherwise, successive washings would soon destroy the efficacy of the material. The plasticizer should not be fugitive, i.e., it should have an extremely low vapor pressure, e.g., below $10^{-9}$ microns Hg. When used, the plasticizer imparts to the final product a desired value of internal viscosity and softness not inherent in those elastomers with which the plasticizer is used. If a copolymer of vinyl chloride and vinyl acetate is used, somewhat less plasticizer is preferred.

Almost any non-water-soluble elastomer will give satisfactory results if formulated in the manner described herein. The high-molecular weight vinyl chloride plastics have the advantages of low cost, ease of handling, transparency, low surface free energy, and a non-linear stress-strain curve.

The adhesive composition may also include tackifiers, antioxidants, antibiotics, antimicrobial agents and the like in effective amounts known to those of ordinary skill in the art.

What is claimed is:

1. An ostomy appliance or wound drainage device comprising:
    (a) a receptacle for storing waste material therein;
    (b) a first opening in the receptacle for receiving waste material from a patient;
    (c) a second opening in a lower end of the receptacle for releasing the waste material from the receptacle; and
    (d) adhesive means on the lower end of the receptacle enabling the lower end of the receptacle to be folded and releasably adhered to itself to thereby close off said opening.
2. The device of claim 1 wherein the adhesive means comprises a washable adhesive.
3. The device of claim 1 wherein the adhesive means comprises the lower end of the receptacle being made of an adhesive material having intrinsic adhesive properties.
4. The device of claim 3 wherein the adhesive material is washable.
5. The device of claim 1 comprising a tube extending from the receptacle and in fluid communication therewith, said tube having an upper end in proximity to the receptacle and a lower end remote from the upper end with a central region therebetween, said tube further having an inner surface and an outer surface and an adhesive layer on at least one of said inner and outer surfaces whereby when the tube is bent in the central region the tube will remain in a folded-over condition sufficient to prevent the flow of fluid therethrough.
6. The device of claim 5 wherein the tube is made of an adhesive material having intrinsic adhesive properties.
7. The device of claim 5 wherein the adhesive layer is on the exterior surface of the tube, whereby the lower end of the tube releasably adheres to the upper end of the tube when the tube is in the folded-over condition.
8. The device of claim 5 wherein the adhesive layer is on the inner surface of the tube.
9. The device of claim 8 wherein the inner surface is comprised of opposed walls, said adhesive layer being on at least one of said walls.
10. The device of claim 9 wherein the adhesive layer covers the entire inner surface of the tube at least in the central region of the tube.
11. The device of claim 1 wherein the lower end of the receptacle comprises a first side and an opposed second side, one of said first and second sides having a first adhesive area surrounding said opening, and a second adhesive area adjacent said first adhesive area, wherein said first adhesive area is folded upon itself to form an adhesive seal with the second adhesive area to thereby close off said opening.
12. The device of claim 11 wherein at least a portion of the first adhesive area includes a relatively stiff supporting material.
13. The device of claim 1 wherein the adhesive means comprises an adhesive layer comprising at least two adhesive regions.
14. The device of claim 13 wherein the adhesive regions are separated from each other by a non-adhesive space.
15. The device of claim 13 wherein the adhesive regions are separated from each other by a scoreline.
16. The device of claim 11 further comprising a third adhesive area adjacent the second adhesive area, wherein the lower end of the receptacle is folded upon itself twice so that the third adhesive area is secured to the lower end of the receptacle.
17. The device of claim 16 wherein said receptacle further comprises a fourth adhesive area on the other of said sides, wherein the lower end of the receptacle is folded upon itself twice so that the third adhesive area is releasably secured to the fourth adhesive area and the first adhesive area is releasably secured to the second adhesive area to close off said opening.
18. The device of claim 11 wherein the second opening is at an endpoint of the receptacle, said lower end having a first adhesive area at the end point on a first side of the device and a second adhesive area on a second, opposed side of the device, wherein when the lower end of the receptacle is folded upon itself the first adhesive area is releasably secured to the second adhesive area to thereby close off the second opening.
19. The device of claim 11 further comprising a third adhesive area on a second, opposed side of the device wherein the lower end of the receptacle is folded upon itself twice so that the first adhesive area is releasably secured to the second adhesive area and the third adhesive area is secured to the lower end of the receptacle.
20. The device of claim 19 wherein the third adhesive area is an adhesive layer applied to the opposed side of the device.
21. The device of claim 19 wherein the third adhesive area comprises a region of the device made of a material having intrinsic adhesive properties.
22. The device of claim 1 wherein the lower end of the receptacle comprises a first side and an opposed second side, and a bottom end having a second opening therein between the first and second sides, one of said first and second sides having a first adhesive area and a second adhesive area adjacent thereto wherein said lower end is folded upon itself so that the first adhesive area forms an adhesive seal with the second adhesive area to thereby close off said second opening.
23. The device of claim 22 further comprising a third adhesive area adjacent the second adhesive area, wherein the lower end of the receptacle is folded upon itself twice so that the third adhesive area is secured to the lower end of the receptacle.
24. The device of claim 23 wherein said receptacle further comprises a fourth adhesive area on the other of said sides, wherein the lower end of the receptacle is folded upon itself twice so that the third adhesive area is releasably secured to the fourth adhesive area and the first adhesive area is releasably secured to the second adhesive area to close off said opening.

25. The device of claim 22 further comprising a third adhesive area on a second, opposed side of the device wherein the lower end of the receptacle is folded upon itself twice so that the first adhesive area is releasably secured to the second adhesive area and the third adhesive area is secured to the lower end of the receptacle.

26. The device of claim 22 wherein the second opening is at an endpoint of the receptacle, said lower end having a first adhesive area at the end point on a first side of the device and a second adhesive area on a second, opposed side of the device, wherein when the lower end of the receptacle is folded upon itself the first adhesive area is releasably secured to the second adhesive area to thereby close off the second opening.

27. The device of claim 1 wherein the adhesive means comprises at least one thermoplastic elastomer.

28. The device of claim 27 wherein the thermoplastic elastomer is a styrene copolymer or an acrylic resin.

29. The device of claim 28 wherein the styrene copolymer is selected from the group consisting of styrene-acrylonitrile-butadiene, styrene-butadiene-styrene, styrene-isoprene-styrene and styrene-ethylene/butylene-styrene.

30. The device of claim 29 wherein the styrene copolymer is a styrene-isoprene-styrene copolymer or a styrene-acrylonitrile-butadiene copolymer having a relatively high butadiene content.

31. The device of claim 28 wherein the styrene copolymer is combined with an oil to form a gel.

32. The device of claim 1 wherein the adhesive composition comprises an elastomeric composition having a modulus of elasticity sufficient to enable waste particles to be readily removed therefrom, and having an internal viscosity low enough to enable water-washing and high enough to provide tack.

33. The device of claim 32 wherein the modulus of elasticity is from about 1 to 100 psi and the internal viscosity is from about 1,000 to 20,000 poises.

34. The device of claim 33 wherein the adhesive composition further comprises a plasticizer.

35. The device of claim 33 wherein the adhesive composition is solid, hydrophobic and insoluble in water.

36. The device of claim 33 wherein the adhesive composition comprises high molecular weight polyvinyl chloride.

37. The device of claim 33 wherein the adhesive composition comprises a copolymer of vinyl chloride and vinyl acetate.

* * * * *